United States Patent
Kreutz et al.

(10) Patent No.: US 7,144,391 B1
(45) Date of Patent: Dec. 5, 2006

(54) FEMININE HYGIENE KIT

(75) Inventors: Karen A. Kreutz, Cincinnati, OH (US);
Lisa A. Mackay, Cincinnati, OH (US);
Donna R. Hill, Erlanger, KY (US);
Thomas W. Osborn, III, Cincinnati, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 869 days.

(21) Appl. No.: 09/653,012

(22) Filed: Sep. 1, 2000

(51) Int. Cl.
*A61F 13/15* (2006.01)
*A61F 13/20* (2006.01)

(52) U.S. Cl. .................... 604/385.17; 604/385.18; 604/904

(58) Field of Classification Search ............... 604/358, 604/904, 385.17, 385.18; 206/225–226, 206/438, 440, 570, 574, 581; 132/286
See application file for complete search history.

(56) References Cited

U.S. PATENT DOCUMENTS

| | | | |
|---|---|---|---|
| 2,938,519 A | | 5/1960 | Marco |
| 3,971,378 A | | 7/1976 | Krantz |
| 5,046,620 A | | 9/1991 | Barabino |
| 5,167,345 A | * | 12/1992 | Bleeker ..................... 221/17 |
| 5,579,916 A | * | 12/1996 | Manko ...................... 206/581 |
| 5,603,685 A | | 2/1997 | Tutrone, Jr. |
| 5,731,083 A | | 3/1998 | Bahia et al. |
| 5,827,251 A | | 10/1998 | Moder et al. |
| 5,891,127 A | * | 4/1999 | Moder et al. ............... 604/358 |
| 5,986,165 A | * | 11/1999 | Moder et al. ............... 604/358 |
| 5,988,386 A | * | 11/1999 | Morrow ..................... 206/581 |
| 6,071,259 A | | 6/2000 | Steiger et al. |
| 6,090,038 A | | 7/2000 | Zunker et al. |
| 6,093,027 A | | 7/2000 | Unger et al. |
| 6,164,442 A | * | 12/2000 | Stravitz .................... 206/233 |
| 6,183,456 B1 | | 2/2001 | Brown et al. |

FOREIGN PATENT DOCUMENTS

| | | |
|---|---|---|
| DE | 9312949.1 U1 | 6/1994 |
| EP | 0072005 A1 | 2/1983 |
| FR | 2703244 A1 | 10/1994 |
| GB | 2277447 A | 11/1994 |
| WO | WO 98/20825 A1 | 5/1998 |
| WO | WO 98/57610 A1 | 12/1998 |

OTHER PUBLICATIONS

Heppermann, Christine M., "Laughing in the Face of Puberty: Books About Sex", Horn Book Magazine (IHBO), vol. 76, No. 2, pp. 162-168, p. 7, Mar./Apr. 2000.
Artis, Elizabeth Goodman, "Tight-Fitting Clothing Can Cause Yeast Infections", COSMOPOLITAN, 226, 6, 82(1), Jun. 1999.
Neubardt, Selig, "Body Parts: Isn't It Time You Figured Out Yours?", COSMOPOLITAN, vol. 221, No. 1, p. 138(2), Jul. 1996.

\* cited by examiner

*Primary Examiner*—Michele Kidwell
(74) *Attorney, Agent, or Firm*—Matthew P. Fitzpatrick; Ken K. Patel; Steven W. Miller

(57) ABSTRACT

Kits of feminine hygiene products are disclosed. In particular, kits which may be used as learner kits are disclosed. Such kits preferably include at least an absorbent tampon having an absorbency of less than or equal to about 6 grams according to the syngina test. Also included are a backup feminine hygiene article such as a pantiliner, sanitary napkin, or absorbent interlabial device. Other optional components such as a mirror, finger cover, glove, lubricant, bonus product, an instruction booklet, may also be included in the kit. Also disclosed are non-absorbent training tampons which may be used to assist a new tampon user in getting the feel for proper tampon insertion technique.

5 Claims, 6 Drawing Sheets

FEMININE HYGIENE KIT

FIELD OF THE INVENTION

This invention relates to feminine hygiene kits. More particularly, the invention relates to improved tampon kits designed for females first learning to use tampons. These kits provide an enhanced first-time usage experience which increases the acceptance of tampon use and makes repeat usage significantly more likely than if first time tampon use is attempted without such kits.

BACKGROUND OF THE INVENTION

A wide variety of absorbent catamenial tampons have long been known in the art. Most currently commercially available tampons are made from a tampon pledget which has been compressed into a substantially cylindrical form. Tampon pledgets of a variety of types and constructions have been described in the art. Prior to compression, the pledget may be rolled, spirally wound, folded, or assembled as a rectangular pad of absorbent material. Tampons made from a generally rectangular pledget of absorbent material as well as tampons made from rolled absorbent material have been popular and successful in the market. The absorbent catamenial tampons now in use typically comprise absorbent members which are compressed to a generally cylindrical or "bullet" shaped form.

First time use of these currently available tampons is often a very difficult and traumatic experience especially for a young woman or girl. The insertion process is often painful and cannot easily be accomplished because she may not be sufficiently familiar with her body. First time trying of tampons may also be messy because the user is usually menstruating. The additional time needed to insert a tampon for the first time during such menstruation has been found to be a source of anxiety among many inexperienced tampon users.

Practicing tampon insertion during non-menstrual times has not been practical for several reasons. Currently available absorbent tampons are not designed to be worn during non-menstrual times in a woman's cycle and such use would not be in accordance with labeling instructions for these tampons. Additionally, removal of a dry or nearly dry tampon is quite uncomfortable as the absorbent material sticks to the vaginal tissues causing pain.

Because of these difficulties, tampon usage has often required a significant degree of perseverance during the learning process. This learning process is often associated with an underlying fear of a painful or uncomfortable experience. It has been found during development of the present invention that many women do not become regular tampon users because of the difficulties associated with the learning process. This is so even though many of these same women indicate a willingness or desire to use tampons because of the advantages such products offer these women over other forms of menstrual protection.

A need, therefore, exists to provide products which may be used by first time or novice tampon users. These products ideally should facilitate establishment of an insertion routine that a given user finds comfortable in a minimum amount of time and with little or no discomfort during this learning process.

Some attempts have been made in the prior art to provide tampon kits. For example, U.S. Pat. No. 5,827,251 issued to Moder et al. describes generally a feminine sanitary protection kit having a pantiliner and a vaginal insertion device. A tampon may be included with the packages described in the Moder et al. patent. The packages of products described in Moder et al. however, are unsuitable for use as a tampon learner kit of the present invention. Moder et al. describes only tampons of the "regular," "super," and "super plus" absorbency ranges. For reasons more fully described herein, these higher absorbency tampons are particularly unsuited for preferred learner kits of the present invention. Additionally, the products described in the Moder et al. patent fail to provide kits which have some of the learning and insertion aids of preferred kits of the present invention such as a mirror, an insertion guide, or a bonus product offering.

An attempt in the prior art to provide an insertion guide is described generally in U.S. Pat. No. 6,071,259 issued to Steiger et al. The Steiger et al. patent generally describes an optional inserter for digital tampons which is described as useful as a training device for new users. The device described in the Steiger et al. reference, however, lacks the advantages of the insertion guide of the present invention. For example, the Steiger et al. device provides no assistance to a user in properly orienting the tampon for insertion. In other words, no assistance is provided by way of assisting the user in achieving an optimal insertion angle, depth, etc.

SUMMARY OF THE INVENTION

This invention relates to feminine hygiene kits and training tampon devices. The feminine hygiene kits of the present invention are particularly suited for use as learner kits for new or novice tampon users. In one embodiment, a kit of the present invention comprises an absorbent tampon and a backup feminine protection product packaged in a common package. The absorbent tampon comprises an absorbent core and a withdrawal mechanism attached to the absorbent core. The absorbent core has a syngina absorbent capacity of less than or equal to about 6 grams. In preferred embodiments, the backup feminine protection product may comprise a pantiliner, a sanitary napkin, or an absorbent interlabial device. In particular preferred embodiments, the backup feminine protection product may comprise a pantiliner having a caliper of less than or equal to about 3 mm.

This invention relates to tampon kits and training tampon devices. In one embodiment, a kit of the present invention comprises an absorbent tampon and a pantiliner packaged in a common package. The absorbent tampon comprises an absorbent core and a withdrawal mechanism attached to the absorbent core. The absorbent core has a syngina absorbent capacity of less than six grams. A kit of the present invention may preferably contain a mirror with the tampon and backup feminine protection product.

In an additional embodiment, a kit of the present invention comprises an absorbent tampon and a mirror. Preferably, kits of the present invention may comprise a tampon insertion guide. Preferably these kits may also comprise a vaginal lubricant. Kits of the present invention may preferably also comprise an insertion glove. Such an insertion glove may preferably also be used as a disposal wrapper for the tampon. The feminine hygiene kit may preferably contain a finger cover. This finger cover may also preferably be also used as a disposal wrapper for the tampon. Preferably, kits of the present invention may also comprise a bonus product offering. Such a bonus product offering may include candy or a bath product. Such a bonus product offering may also include a coupon, including a coupon which may be redeemed in conjunction with women's health services.

A kit of the present invention may also preferably contain an instruction booklet. Preferably, such an instruction booklet comprises instructions which assist a consumer in creating a tampon usage system.

In an additional embodiment, the present invention comprises a training tampon. The training tampon is generally cylindrically shaped and has an insertion end and a withdrawal end. The tampon has a withdrawal mechanism attached to the withdrawal end of the tampon device. The tampon device is configured for insertion into the vaginal canal of a female wearer. The tampon device is substantially non-absorbent. In preferred embodiments, the non-absorbent tampon may be made of a material selected from the group consisting of: teflon, polyethylene, polypropylene, and polyester. Preferably, the training tampon may be housed in an applicator comprising a holder tube and a plunger tube. The holder tube and the plunger tube are telescopically disposed relative to one another. The training tampon may also preferably comprise a vaginal lubricant disposed on the outer surface of the tampon.

Another embodiment of a kit of the present invention may comprise a training tampon in combination with a vaginal lubricant.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

This present invention is directed to feminine hygiene kits and training tampons. The feminine hygiene kits of the present invention are particularly suited for use as learner kits. These kits provide an enhanced first-time tampon usage experience which increases the acceptance of tampon use and makes repeat usage significantly more likely than if first time tampon use is attempted without such kits.

Figure 1:
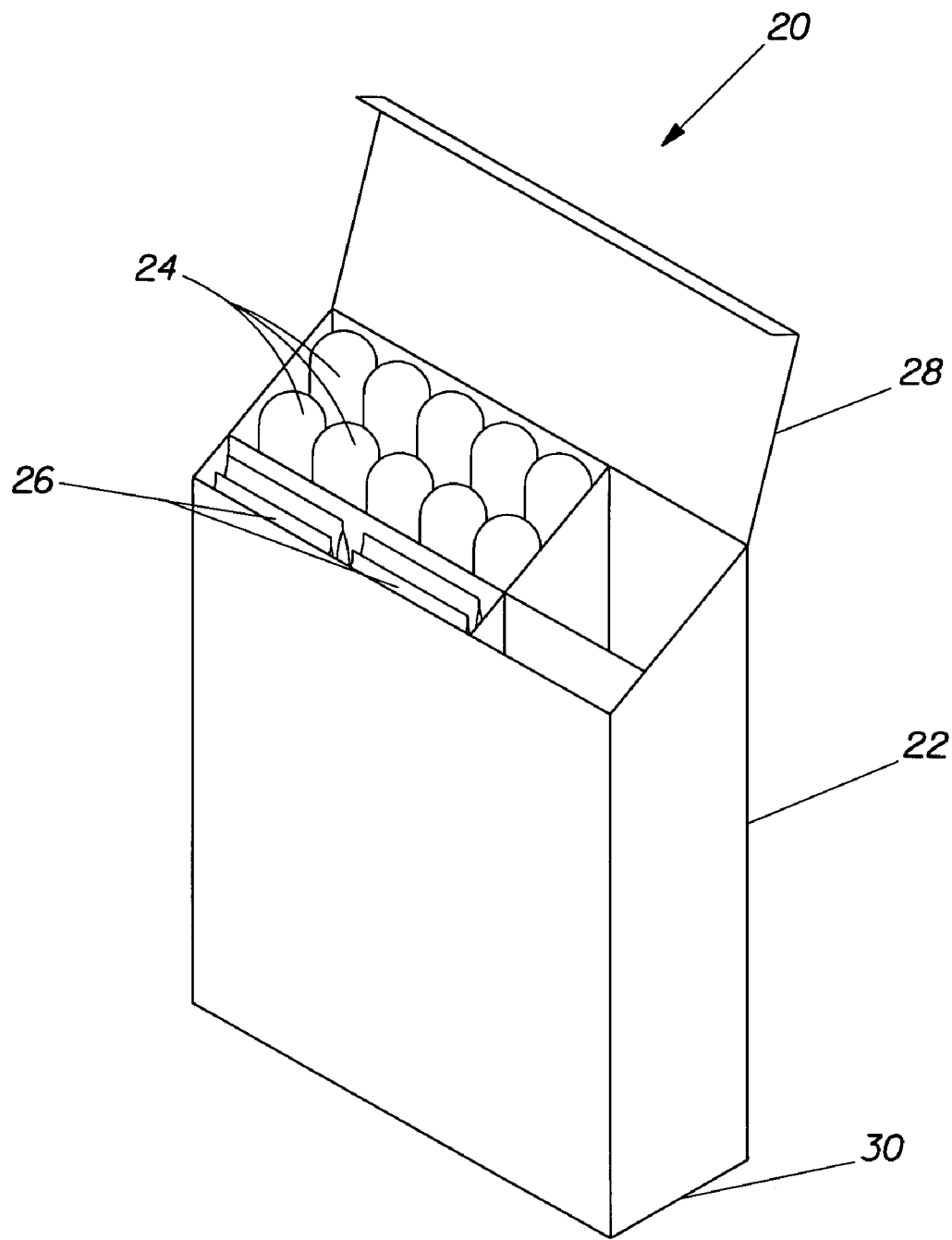
FIG. 1 is a feminine hygiene kit of the present invention.

FIG. 1 shows one embodiment of a feminine hygiene kit 20 of the present invention. In its simplest form, this embodiment of the tampon kit 20 may preferably be thought of as an outer package 22 housing the individual components of the kit. Preferably, the contents of the kit 20 comprise at least one tampon 24 and at least one backup feminine protection product, such as pantiliner 26. The tampon 24 and the pantiliner 26 may be packaged together in the outer package 22 in any suitable manner. For example, in the preferred embodiment shown in FIG. 1, the outer package 22 has a "flip top" lid 28 with a sloped bottom surface 30. Neither of these features is necessary, but such allow the different products to be arranged in a staggered configuration for easy removal of the desired product type. The outer package 22 may generally be in the shape of a box typically used for crayon packaging. As noted, this configuration allows the various individual items to be grasped easily and removed.

The outer package 22 may be re-closeable. Preferably, the outer package 22 is configured such that at least one of type of item which comprises the kit 20 is simultaneously visible and easily graspable by a user. The outer package 22 need not have any particular design feature, however, and may simply consist of a convenient common package in order to contain the items of the kit 20 together for single unit sale.

In the kit shown in FIG. 1, the individual components of the kit 20, such as tampon 24 and pantiliner 26 may each be placed in their own compartment contained within the outer package 22. It is not necessary that such compartments be provided, however, and the components may simply reside within a common outer package. The compartments if provided may take the form of dividers, sleeves within the outer package 22, or any other suitable spacing means. The outer package 22 may be manufactured from cardboard, a polymer bag or film, shrink wrap, or any other suitable material conventionally used for consumer product packaging. Such methods of packing multiple consumer items are generally within the ability of one of ordinary skill in the art. Preferably, the packing is selected to maintain as clean and hygienic condition of the individual products as is possible.

Attention is now turned to the individual items which may comprise a feminine hygiene kit of the present invention. It is to be noted that not all embodiments of the present invention must have an items of each of the types specified and described herein. The various items may be mixed and matched in various combinations in order to obtain a kit of the present invention as described in the present specification and appended claims.

Figure 2:
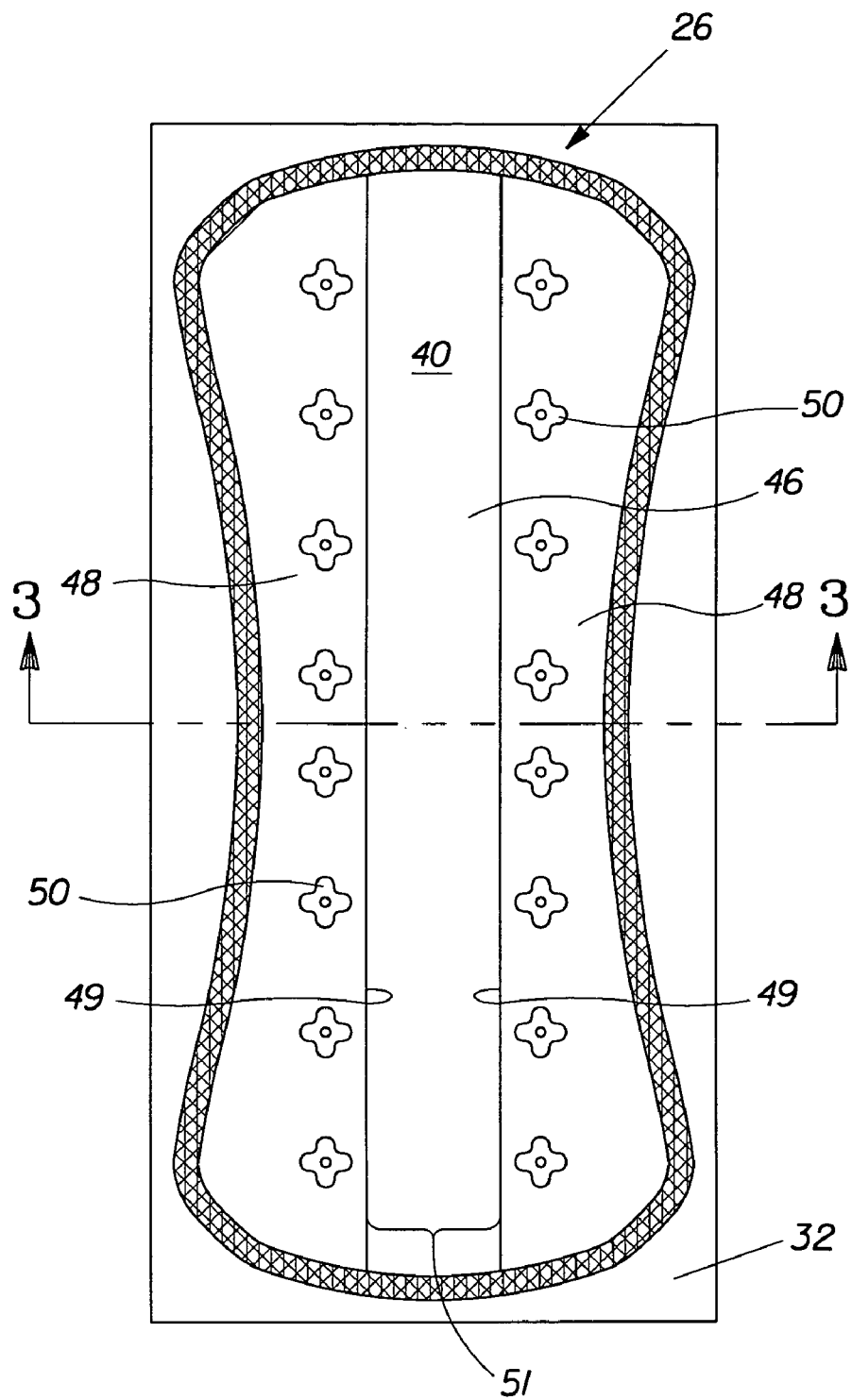
FIG. 2 is a top plan view of a pantiliner which may be incorporated into a kit of the present invention.
Figure 3:
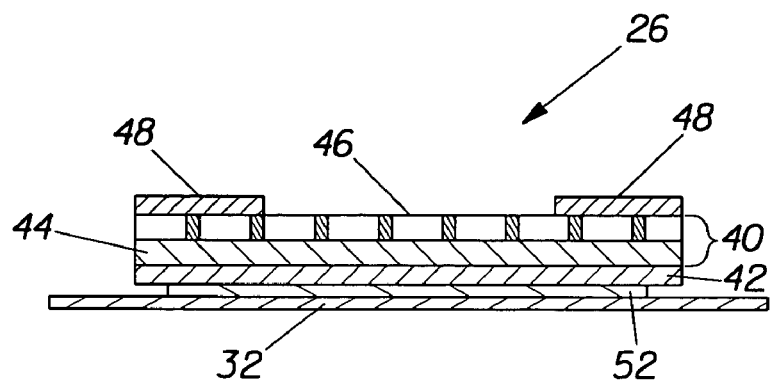
FIG. 3 is a cross sectional view taken along line 3—3 of the pantiliner of FIG. 2.

FIG. 2 shows a top plan view of a preferred pantiliner 26 which may be incorporated into the kit 20 of the present invention. Any suitable conventional pantiliner may be used in the kit 20 of the present invention. The individual components of the preferred pantiliner 26 of the present invention are more clearly seen in FIG. 3. As shown in FIG. 3, the preferred pantiliner 26 has a liquid pervious topsheet 40, a liquid impervious backsheet 42, and an absorbent core 44 positioned between the topsheet 40 and backsheet 42. The pantiliner 26 shown has a "dog bone" shape, but may also have an "hourglass" shape, a "racetrack" shape, an oval shape, or any other suitable shape.

The pantiliner 26 shown in FIGS. 2–3 is preferably releaseably adhered (such as with pressure sensitive adhesive 52) to and wrapped with a release wrapper 32. Preferably, the topsheet is a "hybrid" type topsheet 40 comprising an apertured formed film 46 and nonwoven 48 layers. A suitable pantiliner incorporating such a hybrid topsheet is described in PCT Publication WO 93/09744, published May 27, 1993, in the name of Sugahara, the entire disclosure of which is hereby incorporated by reference.

Preferably, the apertured formed film covers the entire body facing surface of the pantiliner. The nonwoven layer may preferably comprise two strips 49 positioned laterally outboard of a central zone 51. Such central zone 51 has the apertured form film layer directly exposed to the body facing surface of the pantiliner. These apertured form film layers and nonwoven are preferably joined by discrete bonds such as bonds 50. Of course, a hybrid topsheet configuration is not necessary, and a suitable topsheet may be made entirely from a suitable formed film, an apertured or non-apertured nonwoven web, a woven web, or any other suitable body side liner.

The pantiliner 26 may be preferably packaged in a tri-folded release paper wrapper configuration which conserves space within the outer package 22 of the kit 20 of the present invention. An example of folded release paper wrapper configuration is described in U.S. Pat. No. 4,556,146 issued to Swanson et al., the entire disclosure of which is hereby incorporated by reference. A suitable pantiliner for use in the kit of the present invention is manufactured by Procter & Gamble GmbH of Crailsheim, Germany, a subsidiary of The Procter & Gamble Company of Cincinnati, Ohio, and sold under the name ALLDAYS Breathable Singles. Additionally, any of the ALLDAYS pantiliners manufactured by Procter & Gamble are suitable for inclusion in kits of the present invention. Preferably, pantiliners included have a caliper of less than or equal to about 3 mm. A suitable method of determining all caliper measurements given herein is using an AMES gauge with a 0.25 psi (1.7 kPa) load and a 0.96 inch (2.44 cm) diameter foot. One of skill in the art will recognize that if a 0.96 inch (2.44 cm) diameter foot is not appropriate for a particular size of sample, the foot size may be varied while the load on the gauge is varied accordingly to maintain a confining pressure of 0.25 psi (1.7 kPa).

Figure 4:
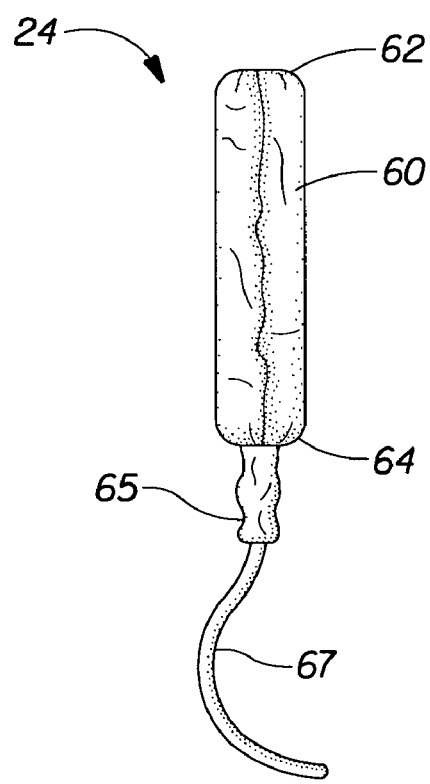
FIG. 4 is an absorbent tampon which may be incorporated into a kit of the present invention.

The kit 20 of the present invention also preferably includes an absorbent tampon 24 such as tampon 24 shown in FIG. 4. As used herein the term "tampon" refers to any type of absorbent structure which is inserted into the vaginal canal or other body cavities for the absorption of fluid therefrom.

Typically, tampons are constructed from an absorbent material which has been compressed in either the radial direction, the axial direction, or both in order to provide a tampon which is of a size and stability to allow insertion within the vagina or other body cavity.

The primary absorbent member 60 (sometimes also referred to as the "absorbent core") of the tampon 24 shown in FIG. 4 has an insertion end 62 and a withdrawal end 64. The primary absorbent member 60 may be compressed into a generally cylindrical configuration in the radial direction or in both the radial and axial directions. While the primary absorbent member 60 is preferably compressed into a substantially cylindrical configuration, other shapes are also possible. These may include shapes having a cross section which may be described as rectangular, triangular, trapezoidal, semi-circular, or other suitable shapes. A withdrawal mechanism such as withdrawal cord 67 is preferably attached to the primary absorbent member 60.

The tampon prior to compression may be any suitable shape, size, material, or construction. In the embodiment shown in FIG. 4, the tampon is formed from a batt of absorbent material which is a generally rectangular pad of absorbent material.

While the tampon 24 shown in FIG. 4 was formed from a generally rectangular absorbent material, other shapes such as trapezoidal, triangular, hemispherical, and chevron shaped are also acceptable. The tampon 24 may be a laminar structure comprised of integral or discrete layers. The tampon may comprise outer layers and at least one intermediate layer positioned between the outer layers. In other embodiments, the pad need not have a layered structure at all. The tampon may comprise a folded structure, may be rolled, may comprise a "petal" structure or any other of the structures which are known in the art with respect to tampon pledgets. The tampon may include a mass of secondary absorbent material 65 or "tail" such as that described in co-pending and commonly assigned U.S. application Ser. No. 09/309,467, filed on May 10, 1999, the entire disclosure of which is hereby incorporated by reference.

The tampon 24 may be constructed from a wide variety of liquid-absorbing materials commonly used in absorbent articles such as rayon, cotton, or comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; or any equivalent material or combinations of materials, or mixtures of these. Preferred absorbent materials comprise cotton, rayon (including tri-lobal and conventional rayon fibers, and needle punched rayon), folded tissues, woven materials, nonwoven webs, synthetic and/or natural fibers.

A suitable process for forming the tampon shown in FIG. 4 is known as carding. Other techniques include as airlaying, wetlaying, or other known techniques. The tampon may preferably be constructed from cotton fibers, rayon fibers, or a blend of these. Depending on the desired absorbency desired in the finished tampon the basis weight of the absorbent material may vary. The United States Food and Drug Administration (FDA) has a set of absorbency standards used throughout the tampon industry. According to these standards, tampons with an absorbency of between 12–15 grams are designated as "super plus." Tampons with an absorbency of between 9–12 grams are designated as "super." Tampons with an absorbency of between 6–9 grams are designated as "regular." Tampons with an absorbency of less than 6 grams are designated as "junior" absorbency.

All of the absorbency ranges given herein are those as measured by the sygyna test as mandated by the FDA, a description of which is reproduced in the "Test Methods" section, below. Preferably, the tampon 24 of the present invention is of the "junior" absorbency type. This absorbency level is also sometimes referred to as "lites" or "light absorbency." A suitable tampon of this type is manufactured and sold by the Procter & Gamble Company of Cincinnati, Ohio as TAMPAX LITES. Such a tampon may preferably have a basis weight of about 438 $g/m^2$, and be constructed from a rectangular absorbent pad comprising 100% cotton. The pad may have an initial length of about 76 mm, and an initial width of about 45 mm prior to compression. The absorbent pad is compressed to its final form, such as that shown in FIG. 4 by temperature and pressure using techniques that are well known in the art.

Tampons of the higher absorbency ranges such as regular, super, and super plus, have previously been disclosed as being packaged with pantiliners such as those which may be included in the kit 20 of the present invention. Nevertheless, it has not been known to package tampons having an absorbency of less than about 6 grams as measured by the syngina test in kits with pantiliners for use as a learner's kit. The use of low absorbency tampons (i.e. below 6 grams, or "junior" absorbency) offers a variety of non-obvious advantages, particularly for the novice user. Therefore, these "junior" absorbency tampons are particularly suited for inclusion in kits of the present invention.

It has been found during development of the present invention that first time or novice tampon users are often highly concerned about accidental soiling and of an unpleasant or uncomfortable insertion experience. Because of the concern of accidental soiling, first time and novice users often tend to try the use of a tampon at "low risk" times in their cycle. Such a time typically includes days when menstrual flow is light such as when it is first starting. Additionally, because of the fear of soiling or pre-mature leakage, such users may also tend to seek a higher absorbency product such as a "super," "super plus" or even a "regular" absorbency tampon. Such a combination of light flow and higher absorbency often leads to an uncomfortable insertion experience, however.

If the tampon is not saturated when it is removed, the dry fibers of the tampon have a tendency to adhere to the naturally moist surfaces of the vaginal canal. In such a situation, removal of the tampon is quite uncomfortable. Surprisingly, it has been found that discomfort associated with the removal of one tampon will contribute to an uncomfortable insertion experience with respect to insertion of a replacement tampon. This is particularly true because novice and first time users often have a tendency to remove the tampon shortly after insertion in order to minimize the risk of premature leakage or accidental soiling.

The novice or first time user, then, in order to minimize the risk of leakage, tends to want to use more absorbency than might be necessary at the time when flow may be the lightest for her. This is particularly true for teens or young users who may tend to have lighter flow and smaller bodies in the first instance.

The learner's kit of present invention, by providing a tampon having an absorbency in the range of less than or equal to about 6 grams offers several advantages. Firstly, such tampons because-they are less absorbent that other tampons typically require less absorbent material, and are therefore generally smaller than higher absorbency tampons. Such smaller size contributes to insertion and removal comfort. Additionally, because they do not remain "dry" for as long as higher absorbency tampons, they will tend to be more comfortable upon removal (and even insertion) for newer users who will tend to use the kit of the present invention during times of low flow.

The backup feminine protection product, such as a pantiliner, which may be provided with the kit of the present invention is included in order to address the concern which the novice or first time tampon user may have with using low absorbency tampons as well as to provide additional re-assurance. For example, a pantiliner, such as pantiliner 26 provides reassurance to the user that a junior absorbency tampon may be used without fear of leakage or soiling because the pantiliner is available to absorb any flow which may accidentally leak past the tampon. This also provides some comfort to the new user who may take more time than an experienced tampon user during the insertion process. The pantiliner reduces the anxiety that leakage may occur during the time the user is trying to get the tampon inserted properly.

A backup feminine protection product also allows for new users to feel comfortable using lower absorbency tampons during times of moderate menstrual flow. Therefore, in preferred executions of the kit of the present invention, the kit includes instructions (such as within an instruction booklet discussed in more detail below) suggesting that the user first insert the included tampons during times of moderate menstrual flow. Such a use will result in a more comfortable insertion experience, and therefore, encourage repeat usage. The provision of the backup product increases the likelihood that such an instruction suggestion will be complied with by users of the kit.

Another benefit of a backup feminine protection product such as pantiliner 26 is that encourages the first time or novice user to wear a tampon of the kit for a sufficient length of time. In the absence of such a backup product, a new user may have a tendency to remove the tampon more quickly, resulting in the discomfort referenced earlier.

Pantiliners, such as pantiliner 26 are preferred as the product form for use as the backup feminine protection product within kits of the present invention. One reason for this is that pantiliners have a lower wearing awareness than other feminine protection product forms. For example, sanitary napkins, which are relatively more bulky that pantiliners may tend to be noticed by a consumer during wear. This may lead a consumer to come to rely on a "reassurance" provided by feeling the sanitary napkin. This can detract from the effectiveness of the kit as an items which assists in promoting acceptance of tampons for regular, as opposed to backup only use.

Preferred pantiliners of the kit 20 of the present invention should be thin, relatively flexible, and need not be highly absorbent. Nevertheless, other types of feminine protection products may serve as the backup product of the present invention. Such product types include, sanitary napkins of both the "ultra" and regular varieties, and absorbent interlabial devices. A suitable sanitary napkin is the ALWAYS® Ultra thin Maxi sanitary napkin which is manufactured and packaged by the Procter & Gamble Company of Cincinnati, Ohio under one or more of U.S. Pat. Nos. 4,342,314, 4,463,045, 4,556,146, 4,950,264, 5,009,653, 5,413,568, 5,460,623, 5,462,166, 5,569,231, and Re. 32, 649. A suitable absorbent interlabial device may be any of the devices described in such U.S. patents as U.S. Pat. Nos. 3,983,873 and 5,762,244 or PCT Publication WO 98/57610, published on Dec. 23, 1998.

Figure 5A:
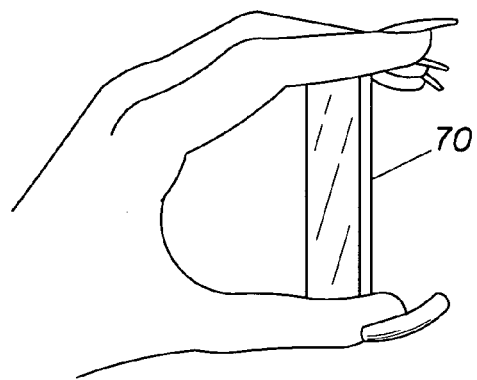
FIGS. 5A–5G show additional items which may be incorporated into a kit of the present invention.

In addition to a pantiliner 26 (or other backup feminine hygiene product) and tampon 24 described above, kits of the present invention may be provided with additional optional components designed to facilitate the tampon learning experience and tampon usage acceptance. For example, the kit shown in FIG. 1 may be provided with a mirror, such as mirror 70 shown in FIG. 5A. A mirror may be used by the user to better see the external genitalia in order to properly position the tampon for insertion. The use of a mirror to better see the body assists the user in understanding her body and often leads to a better experience in using and accepting tampons. Preferably, such a mirror should be compact so that it may be easily manipulated. A hand held mirror, especially one that may be held between the fingers of one hand is ideal for this purpose.

Figure 5B:
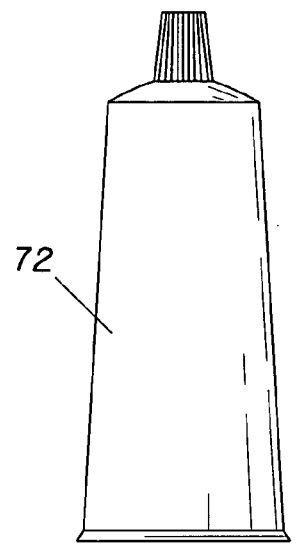
Figure 5C:
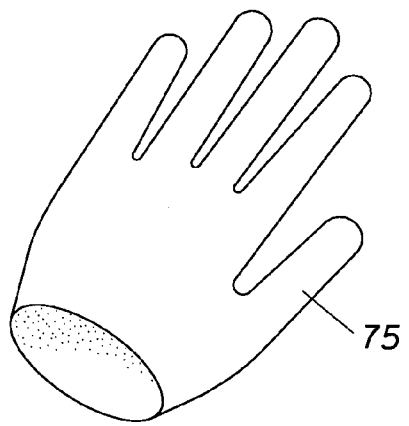
Figure 5D:
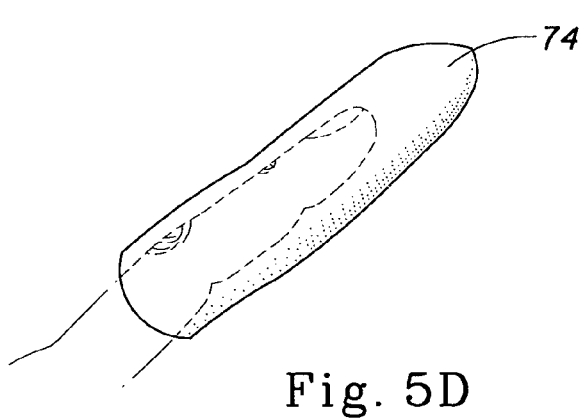

A tube of vaginal lubricant 72, shown in FIG. 5B, may also be included with a kit 20 of the present invention. Any suitable lubricant may be used for this purpose. Such a lubricant may be used to lubricate the tampon, the vagina, or both in order to facilitate a more smooth and comfortable insertion for the user. The lubricant need not be contained in a tube, but may be contained in any suitable container or may be already coated on the surface of the tampon. FIG. SD shows an optional finger cover 74 in the form of a "finger glove" which may also be included. Additionally, other types of finger covers such as absorbent or non absorbent drapes may also be included. Optionally, a glove to cover the entire hand is also suitable. Such a glove, such as glove 75 (FIG. 5C) may be made of latex or other suitable material. The finger glove 74 may be used to protect the finger while allowing the user to feel the vaginal canal with her finger in order to get a better feel for its orientation, size, etc. Either a hand glove or finger cover may also be used as a wrapper for disposal of a used tampon. Also, disposable wipes may be included in kits of the present invention. Wipes are useful as a new user may make several attempts at insertion. Additionally, a glove such as glove 75 or finger cover such as finger glove 74 may be coated with a lubricant either directly or indirectly via micro encapsulation.

Figure 5E:
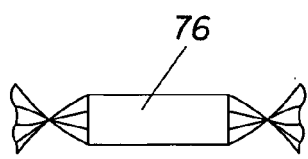
Figure 5F:
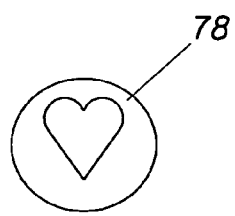

It has also been found during the development of the present invention that providing positive feedback as part of the learning experience is highly effective in establishing tampon use acceptance. Therefore, the kit of the present invention may also be provided with a "bonus product offering." Such a bonus product offering may be intended to serve as a small "reward" to the consumer which she may give herself for successful tampon insertion. Such a reward product offering may be an item which is traditionally associated with feminine hygiene products, in order to enhance its value as a "reward" value. Examples of suitable bonus product offerings include candy 76 (FIG. 5E), a piece of chocolate, a bath product such a bath soap 78 (FIG. 5F), oil, or gel, a candle, or any other suitable product. Other types of offerings may be including which complement the feminine hygiene products included. Such offers may include coupons for tampons or other products which may be used once a user becomes comfortable with the tampon insertion experience and wishes to move beyond a learner type kit. Another beneficial coupon is one that could be used in conjunction with women's health services such as a gynecological exam. It will be apparent to one of skill in the art that the size and configuration of the outer packaging 22 of the kit should be adjusted accordingly to accommodate any such optional kit components which may be included.

Figure 5G:
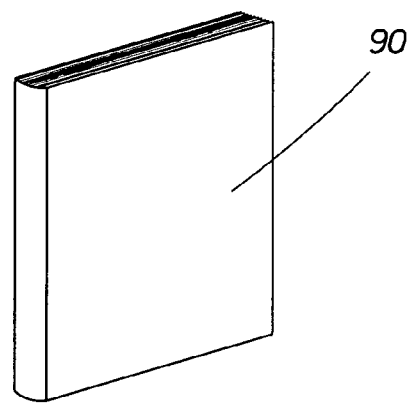

In preferred embodiments, kits of the present invention are provided with instruction booklets 90 such as that shown in FIG. 5G. Such instruction booklets may provide general information of interest on the female anatomy, tampons, how tampons work, how to insert tampons, and related information. Preferably, the information provided is comprehensive in order to alleviate the fear of the "unknown" which many users may experience with respect to first time tampon use. In particularly preferred embodiments, the instruction booklet includes information which will assist the user in making the transition from the learner's kit to more conventional tampon products. For example, when using tampons throughout her menstrual period, a user may have to use multiple absorbencies and a junior absorbency tampon may not always be sufficient. Therefore, the instruction booklet should assist the user in planning for the need to move to different levels of absorbency on higher flow days and as her needs dictate. Ideally, the instruction booklet should offer guidance to the user in formulating a "system" of tampon usage that is right and best for her. Such guidance could be in the form of a chart which allows the user to plot her flow on each day of her menstrual period as "light," "light to medium," "medium to heavy," and "very heavy." This chart could then be indicated as corresponding to Junior (lites), Regular, Super, and Super Plus absorbency tampons, respectively.

The instruction booklet may also be provided with information allowing a user to contact a credible source of information for additional assistance. Such information could include an "800" or other telephone number staffed with representatives who can a assist a new user with using the kit of the present invention. Additionally, phone links, links to a web site, cassette, VCD, CD-ROM, video, or even a small interactive instructional device could also be included.

Figure 6:
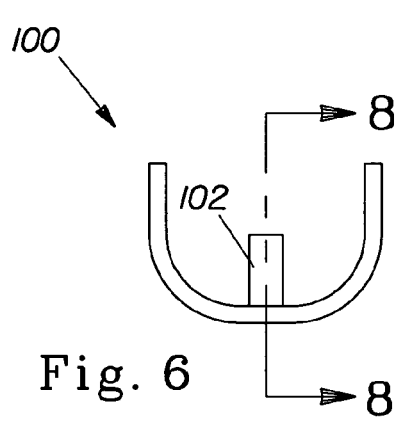
FIG. 6 is a side view of a tampon insertion guide which may be incorporated into a kit of the present invention.
Figure 8:
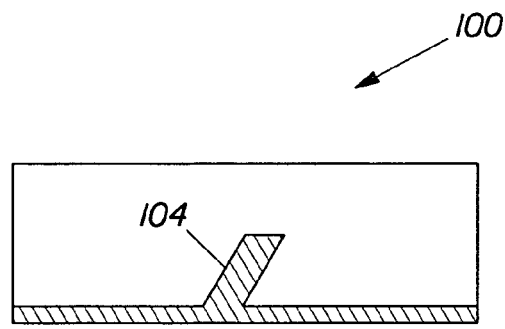
FIG. 8 is a cross-sectional view taken along line 8—8 of the tampon insertion guide shown in FIG. 6.
Figure 7:
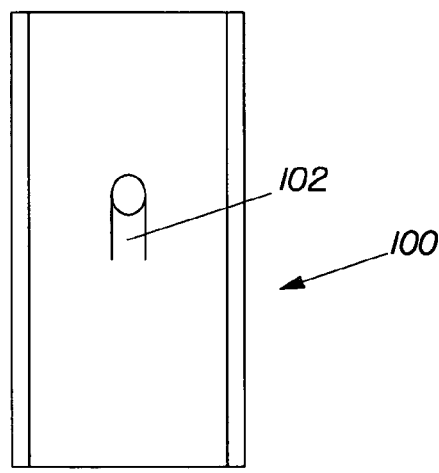
FIG. 7 is a top down view of a tampon insertion guide shown in FIG. 6.

A kit of the present invention may also be provided with an optional tampon insertion guide 100 and example of which is shown in FIGS. 6–8. A tampon insertion guide 100 may be designed to be placed against the body in the genital region. Alternatively, the guide may be used outside the body for practice use. A guide for use against the body 100 may have an opening or hole 102 which has side walls 104 which are angled and/or oriented to assist the user in achieving the correct angle of insertion of the tampon. Such an insertion guide could also be provided with a stop or other mechanism to assist a user in determining an optimal insertion depth for a tampon applicator. It has been found during development of the present invention that many first time or novice tampon users often do not insert the tampon in the optimal direction (i.e. insertion angle) and have to experiment by trial and error. The guide 100 assists the user in getting a "feel" for the proper angle of insertion in order to minimize discomfort associated with the learning process. The tampon insertion guide may be made of any suitable material such as cardboard or plastic.

Figure 9:
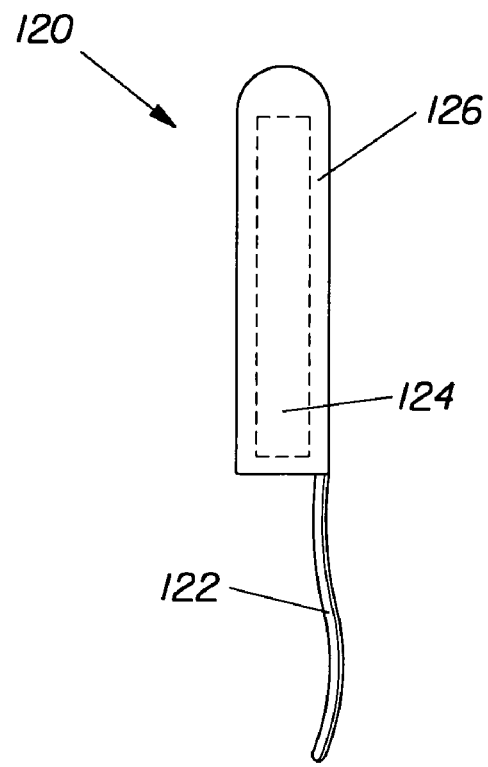
FIG. 9 is a non-absorbent tampon device which may be used as a training tampon of the present invention.

In addition to the absorbent tampons described above, a kit of the present invention may also be provided with a non-absorbent "training tampon." An example of such a training tampon 120 is shown in FIG. 9. The training tampon 120 may be included as part of any of the kits previously described or may be a "stand alone" product. Preferably, the training tampon 120 resembles an absorbent tampon in size and shape as closely as possible. The training tampon 120 should be provided with a withdrawal mechanism, such as withdrawal cord 122. Ideally, the training tampon has a smooth and lubricious surface such that it may be comfortably inserted into the vagina.

The training tampon is preferably non-absorbent such that it may be used during non-menstrual times in order to "practice" tampon insertion. Such non-menstrual practice reduces the anxiety associated with getting the feel of proper tampon insertion during times of actual flow and, therefore, potential leakage.

Figure 10:
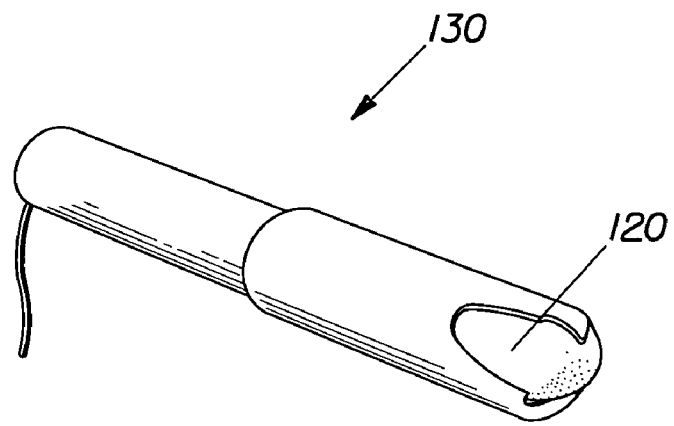
FIG. 10 is a tube and plunger applicator housing the non-absorbent training device shown in FIG. 9.

The training tampon 120 may be made of any suitable material including Teflon, polyethylene, and polyester. Preferably, the training tampon 120 should be flexible or pliable. The training tampon could have a soft core 124 for flexibility surrounded by an outer coating 126 for smoothness. Suitable materials for such a core might include a foam, elastomer, soft rubber, or the like. As shown in FIG. 10, the training tampon 120 may be housed in any suitable "tube and plunger" type applicator 130 or other type applicator. This allows a user to get the most realistic practice with tampon insertion. Alternatively, the training tampon 120 may be inserted digitally if a user wishes to practice this method of insertion. The training tampon 120 may be, but need not be disposable. It may be designed to washed, and/or sterilized and re-used. The training tampon may also be provided with a lubricant either already disposed on the training tampon, or packaged in a tube or other suitable container with the training tampon as part of a kit.

Test Method

Standard Syngyna Test

An unlubricated condom, with tensile strength between 17 Mega Pascals and 30 Mega Pascals is attached to the large end of a glass chamber with a rubber band and pushed through the small end of the chamber using a smooth, finished rod. The condom is pulled through until all slack is removed. The tip of the condom is cut off and the remaining end of the condom is stretched over the end of the tube and secured with a rubber band. A preweighed (to the nearest 0.01 gram) tampon is placed within the condom membrane so that the center of gravity of the tampon is at the center of the camber. An infusion needle (14 guage) is inserted through the septum created by the condom tip until it contacts the end of the tampon. The outer chamber is filled with water pumped from a temperature-controlled waterbath to maintain the average temperature at 27±1° C. The water returns to the waterbath. Syngyna fluid (10 grams sodium chloride, 0.5 gram Certified Reagent Acid Fushsin, 1,000 milliliters distilled water) is then pumped through the infusion needle at a rate of 50 milliliters per hour. The test shall be terminated when the tampon is saturated and the first drop of fluid exits the apparatus. (The test result shall be discarded if fluid is detected in the folds of the condom before the tampon is saturated). The water is then drained and the tampon is removed and immediately weighed to the nearest 0.01 gram. The absorbency of the tampon is determined by subtracting its dry weight from this value. The condom shall be replaced after 10 tests or at the end of the day during which the condom is used in testing, whichever occurs first.

This concludes the Test.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

The disclosures of all patents and patent applications referred to in this specification are hereby incorporated by reference as if fully set forth herein. While particular embodiments of the present invention have been illustrated and described, it would be obvious to those skilled in the art that various other changes and modifications can be made without departing from the spirit and scope of the invention.

The invention claimed is:

1. A feminine hygiene kit comprising:
   an absorbent tampon, said tampon comprising an absorbent core and a withdrawal mechanism attached thereto, wherein said absorbent core has a syngyna absorbent capacity of less than 6 grams, and
   a backup feminine protection product, wherein
   said absorbent tampon and said backup feminine protection product are packaged in a common package and wherein
   said kit further comprises a bonus product offering.

2. The feminine hygiene kit of claim 1 wherein said bonus product offering comprises candy.

3. The feminine hygiene kit of claim 1 wherein said bonus product offering comprises a bath product.

4. The feminine hygiene kit of claim 1 wherein said bonus product offers comprises a coupon.

5. The feminine hygiene kit of claim 4 wherein said coupon may be redeemed in conjunction with women's health services.

* * * * *

UNITED STATES PATENT AND TRADEMARK OFFICE
CERTIFICATE OF CORRECTION

PATENT NO. : 7,144,391 B1  Page 1 of 1
APPLICATION NO. : 09/653012
DATED : December 5, 2006
INVENTOR(S) : Karen A. Kreutz et al.

It is certified that error appears in the above-identified patent and that said Letters Patent is hereby corrected as shown below:

Title Page

Item (73) Assignee: delete "Proctor" and insert -- Procter --.

Column 7

Line 33, delete the hyphen "-" between the words "because" and "they".

Column 8

Line 59, delete "SD" and insert -- 5D --.

Signed and Sealed this

Seventeenth Day of July, 2007

JON W. DUDAS
*Director of the United States Patent and Trademark Office*